United States Patent [19]

Krasnov et al.

[11] 4,354,286

[45] Oct. 19, 1982

[54] ARTIFICIAL EYE LENS

[76] Inventors: Mikhail M. Krasnov, ulitsa Udaltsova, 24, kv. 66; Nikolai N. Pivovarov, ulitsa Nezhinskaya, 15, korpus 3, kv. 87, both of Moscow, U.S.S.R.

[21] Appl. No.: 309,045

[22] Filed: Oct. 6, 1981

[51] Int. Cl.³ .................... A61F 1/16; A61F 1/24
[52] U.S. Cl. ........................................................ 3/13
[58] Field of Search ........................................... 3/13, 1

[56] References Cited

U.S. PATENT DOCUMENTS

| 4,073,015 | 2/1978 | Peyman et al. | 3/13 |
| 4,085,467 | 4/1978 | Rainin et al. | 3/13 |
| 4,257,130 | 3/1981 | Bayers | 3/13 |
| 4,280,232 | 7/1981 | Hummel | 3/13 |
| 4,316,292 | 2/1982 | Alexeev | 3/13 |

FOREIGN PATENT DOCUMENTS

| 563174 | 7/1977 | U.S.S.R. | 3/13 |
| 599806 | 3/1978 | U.S.S.R. | 3/13 |

Primary Examiner—Ronald L. Frinks
Attorney, Agent, or Firm—Fleit & Jacobson

[57] ABSTRACT

According to the present invention the artificial eye lens disclosed herein comprises the supporting element made up of two components, one of which is essentially an arc-shaped loop fixed with its ends in the lens lateral surface. Said loop is situated over at least half the length of the lens circumference and is spaced apart from the lens face surface a distance equal to the thickness of the iris. The other component of the supporting element is made as a U-shaped leg which is also made fast in the lens lateral surface and is arranged oppositely to the middle portion of the loop. The leg is bent towards the loop so as to contact the latter prior to implanting the lens in the posterior eye chamber.

2 Claims, 4 Drawing Figures

ARTIFICIAL EYE LENS

The present invention relates generally to medical engineering.

Artificial eye lenses adapted to be implanted in the posterior chamber of the eye have gained widespread application in the last few years. As a rule such an eye lens prosthesis comprises an optic lens and two supporting legs, a top and a bottom, arranged diametrically opposite on said optical lens and held thereto in its lateral surface, said legs being sutured to the surrounding tissues after the artificial lens has been implanted in the posterior chamber of the eye.

It is expedient that artificial eye lenses be implanted in the posterior chamber of the eye with the presence of an intact posterior lens capsule. The following indications for implanting an artificial eye lens in the posterior chamber of the eye are considered to be the principal ones: the presence of vast anterior synechia, and a shallow anterior chamber of the eye. Implantation is carried out through the pupil, therefore its diameter should not be below 7 mm. However, an artificial eye lens can be implanted via a basal iridotomy should the pupil be impossible to dilatate. After formation of an inferior iridopuncture by resorting to any of the heretofore techniques, and cataract extraction the bottom supporting leg is introduced through the pupil and the iridopuncture previously made so that the distal leg portion should extend completely into the anterior ocular chamber, and the leg elbow-shaped bend should rest against the iridopunctures. A superior iridopuncture is made using the Sato's knife or Wanna's scissors. The upper edge of the pupil is held by forceps and stretched over the top supporting leg so that its distal end should appear through the iridopuncture. If the top supporting leg is not in the hole completely one must catch the leg end with the forceps and pull it slightly upwards.

When implanting an artificial eye lens in the posterior ocular chamber, the fixing of the bottom supporting leg according to the above-mentioned techniques is followed by a horizontal basal iridotomy, whereupon the top supporting leg and the optic lens are placed in the posterior ocular chamber in such a manner that the "earlet" of the top supporting leg should appear within the area where the aforesaid iridotomy has been made. Then a suture is applied through the "earlet" from before backward to prick out through the upper iridotomic lip. The suture is tied up above the iris by two knots and the ends are cut short under a great magnification (10 to 12×) of the operation microscope (cf., e.g., "Implantation of artificial eye lenses with extrapupillary fixation to the iris", Methodical recommendations, Moscow 1977, pp. 22 /in Russian/). As it becomes evident from the above-discussed, implanting an artificial eye lens featuring diametrically opposite supporting legs though yielding good results, however, involves the use of rather complicated surgical equipment on the one hand and cannot prevent a possibility of dislocating the supporting legs from the holes in the iris in the case of atrophic state of the latter, on the other hand.

It is an object of the present invention to provide an artificial eye lens having such a construction that would be capable of its holding in the posterior chamber without stitching up the supporting elements.

It is another object of the present invention to provide such a constructional arrangement of the supporting elements of an artificial eye lens that would ensure simplified implanting techniques of an artificial eye lens irrespective of whether the posterior capsule of the eye lens remains intact, i.e., following both intracapsular and extracapsular cataract extraction.

It is one more object of the present invention to provide higher reliability of fixing the artificial eye lens involved.

It is still more object of the present invention to render the operation less traumatic.

The aforesaid and other objects are accomplished due to the fact that in an artificial eye lens adapted for being implanted in the posterior chamber of a patient's eye and comprising an optic lens and a supporting element made of an elastic material and held to the lateral surface of said lens, according to the present invention, the supporting element is made up of two components of which one is shaped as an arc-like loop made fast with its ends in the lens lateral surface and arranged in front of the lens anterior surface outside the field of view thereof over a length equal to at least half the length of the lens circumference at a distance corresponding to the thickness of the iris, while the other component is made as a U-shaped leg arranged oppositely to the middle portion of the arc-shaped loop and fixed in the lens lateral surface. The both components are bent to contact each other prior to implanting the lens in the posterior chamber.

The herein-proposed artificial eye lens is advantageous in that it makes it possible to simplify the implantation operative techniques as compared to the heretoforeknown artificial eye lenses having two diametrically opposite legs, as the provision of a single supporting element built up of two components simplifies the bringing of the lens into the posterior chamber which is a rather complicated task from a technical standpoint with the previously known artificial lenses in the case of a shallow anterior eye chamber. Moreover, the herein-proposed artificial eye lens dispenses with a possibility of stitching up the supporting element thereof to the iris. The present invention increases the reliability of fixing the artificial eye lens due to the fact that the arc-shaped leg has a large bearing area on the front portion of the iris, whereby the stability of the lens position during lateral displacement of the eye becomes higher, whereas the bent-out leg prevents the lens from being displaced into the anterior eye chamber in the case of pupil dilatation and excludes subsequent jamming of the iris in the case of pupil contraction and, in addition provides for an additional point of the lens fixation.

According to one of the embodiments of the present invention the loop is arranged lengthwise the lens outside surface, while the leg is bent out towards the loop at 15° to 20° with respect to the lens frontal surface.

In what follows the present invention is illustrated by a detailed description of a specific exemplary embodiment thereof which is by no means to bound this invention in any way, to be read with reference to the accompanying drawings, wherein.

Figure 1:
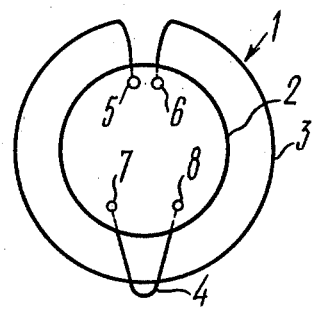
FIG. 1 is a front view of the artificial eye lens, according to the present invention.
Figure 2:
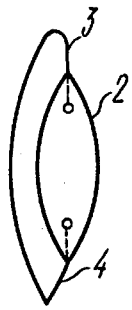
FIG. 2 is a side view of the artificial eye lens, according to the present invention.

Let one make reference first to FIGS. 1 and 2, wherefrom it is evident that the herein-proposed artificial eye lens indicated as a whole at Ref. No. 1 is made up of a lens 2 proper, a loop-shaped component 3 and a U-shaped leg 4 which constitute together a supporting element which enables the artificial lens to be secured in the posterior chamber of a patient's eye without being stitched up to the surrounding tissues as it will hereinafter be described in detail.

The optical lens 2 of the proposed artificial eye lens is of a conventional type and made from an appropriate material compatible with the eye tissues, e.g., from polymethylmethacrylate (proprietary name). As a rule the lens 2 is 5 to 6 mm in diameter.

The loop-shaped component 3 is made of a fine wire or filament from, say, a Pt-Ir alloy or polypropylene (proprietary name), or else from any other material compatible with the eye tissue. Ends 5 and 6 of the loop-shaped component 3 are embedded in the lateral surface of the lens 2. The loop 3 itself, as it can be seen distinctly from FIG. 1 is passed over a length approximately 4/5 that of the circumference of the lens 2 outside the field of view thereof; to this effect the loop 3 somewhat exceeds the lens 2 in the diameter, that is, in this particular case the diameter of the lens 2 is within 5 and 6 mm, whereas that of the loop of the loop-shaped component 3 is within 8.5 and 9 mm. The loop-shaped component 3 is arranged lengthwise or parallel to the lens frontal surface, as it is clearly visible from FIG. 2 and is spaced apart from the lens a distance equal to the thickness of the iris.

Situated oppositely to the middle portion of the loop-shaped component or loop 3 is a U-shaped leg 4 with its ends 7 and 8 made fast in the lateral surface of the lens 2. The leg 4 is bent towards the loop 3 so as to make up an angle of from 15° to 20° with the frontal surface of the artificial eye lens being implanted. In a general case said leg is so bent as to be in contact with the loop 3 before implanting.

The afore-described artificial lens is implanted in the patient's eye as follows.

Figure 4:
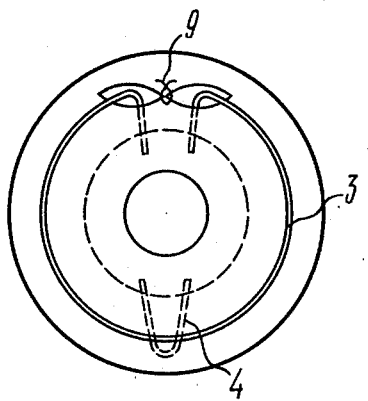
FIG. 4 is a front view of FIG. 3.
Figure 3:
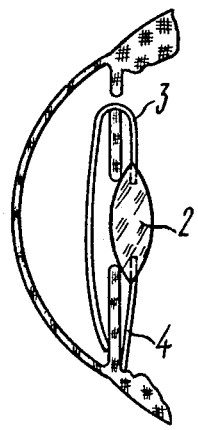
FIG. 3 is a sectional view of the artificial eye lens, according to the present invention, when implanted in the posterior eye chamber.

The anterior eye chamber must be slit open through a keratotomy or keratosclerotomy (FIG. 4). Cataract extraction is done with the help of a cryoextractor or by resorting to the extracapsular method. This done the loop 3 must be caught by suture forceps, and the lens 2 together with the leg 4 is brought into the posterior eye chamber via a basal iridotomy 3.5 to 4 mm spaced 3 mm apart from the pupil margin along the twelve o'clock meridian.

A suture 9 of nylon or supramide (proprietary names) thread is applied to the iridotomy at its centre. It should be noted however that experience has shown such a suture to be dispensed with.

Proper centring of the lens is attained largely due to selecting the place of the iridotomy which can be made in the upper portion of the iris from the limbus to the pupil margin. Preparatory to making iridotomy one must apply the artificial lens (or a spatula graduated in millimeters) to the iris and make an incisure of the iris at a required place with the optical axis of the lens arranged at the centre of the pupil.

Given below are two case histories to illustrate practical application of the proposed artificial eye lens.

1. Patient P-v D.F. Diagnosis: mature cataract of the left eye, immature cataract of the right eye.

Intracapsular cryoextraction of the cataract was carried under local anesthesia with a 2-percent novocain solution. A keratosclerotomy was made, whereupon the cataract was extracted through the pupil. Next a basal iridotomy 3.5 mm long was made 3 mm apart from the margin of the pupil along the twelve o'clock meridian, and an artificial lens was brought through the thus-made basal iridotomy. The lens was held by a suture forceps and introduced tangentially to the anterior boundary membrane of the vitreous body, while the bottom supporting loop and the optical lens were situated under the iris in the posterior eye chamber and the top loop rested upon the peripheral portion of the iris round the pupil. A loop suture was placed on the basal iridotomy using supramide 10-0.

The keratoscleral wound was stitched up by a continuous suture of supramide 10-0, whereupon sterile air was admitted to pass into the anterior eye chamber.

A solution of pencillin was administered under the conjunctiva. The patient was permitted to walk two hours after the operation. The postoperative coursing was uneventful. Application of strong mydriatics (viz. a 0.2-percent scopolamine solution) made it possible to dismiss the patient on the 7th day after the surgery as in the case of a conventional cataract extraction. The acuity of vision was 0.7 to 0.8.

A repeated examination of the patient half a year after the operation demonstrated a stable position of the artificial lens implanted and acute eyesight retained in the patient.

2. Patient R-a, Ye.P. Diagnosis: mature age-dependent cataract of the left eye.

Intracapsular cryoextraction of the cataract was carried out after conventional preoperative procedure and under anesthesia common to a cataract extraction surgery.

A keratosclerotomy was made for the purpose and the cataract was extracted through the pupil.

There was observed pronounced prominence of the vitreous body through the pupil which practically ruled out implantation of a commonly adopted iris-clip lens without considerable loss of the vitreous body. Insertion of the herein-disclosed artificial eye lens through a peripheral basal iridotomy 3.5 mm long made it possible to avoid vitreoptosis as the lens and the bottom supporting loop slided down the anterior boundary membrane of the vitreous body.

In addition, the lens implanting procedure did not involve a considerable opening of the incision which is the case with implanting intrapupillary lenses. The keratotomy wound was stitched up by a continuous suture using supramide thread.

Strong mydriatics were administered within the postoperative period, viz., a solution of scopolamine, which made it possible to avoid postoperative iridocyclitis.

The acuity of eyesight at the patient's dismissal was 0.8 to 0.9.

An examination of the patient in a year showed the lens in a correct position without dislocation of the supporting elements. Acuity of vision retained completely.

Practical application of the present invention is instrumental in considerable simplification of the operative procedure, renders it less traumatic and provides for reliable fastening of an artificial eye lens in the posterior eye chamber.

Disclosed hereinabove has been an optimum embodiment of the artificial eye lens, wherein some modifications may be introduced without departing from the spirit and scope of the present invention. Thus, it is permissible that the arc-shaped loop 3 would pass over a length shorter than 4/5 that of the lens circumference but at least half the length thereof.

What we claim is:

1. An artificial eye lens adapted for being implanted in the posterior chamber of a patient's eye, comprising an optical lens proper and a supporting element made of an elastic material, said supporting element being made up of two components, viz., a first and a second, of which the first component is essentially an arc-shaped loop fixed with its ends in the lens lateral surface and situated in front of the lens surface over a length equal to at least half the length of the lens circumference at a distance from the lens surface corresponding to the thickness of the iris, while the second component is made as a U-shaped leg arranged oppositely to the middle portion of said arc-shaped loop and fixed with its ends in the lens lateral surface; both of the abovesaid components being so inclined as to contact each other prior to implanting the lens in the posterior chamber.

2. An artificial eye lens as claimed in claim 1, wherein the U-shaped leg makes up an angle of from 15° to 20° with the lens frontal surface, while the arc-shaped loop is arranged parallel to the lens face surface.

* * * * *